United States Patent [19]

Nieh

[11] 4,396,519

[45] Aug. 2, 1983

[54] ALKYL-SUBSTITUTED BICYCLOALKYL ETHERS AS USEFUL LUBRICANTS AND LUBRICATING OILS CONTAINING SAID ETHERS

[75] Inventor: Edward C. Y. Nieh, Austin, Tex.

[73] Assignee: Texaco Inc., White Plains, N.Y.

[21] Appl. No.: 362,688

[22] Filed: Mar. 29, 1982

Related U.S. Application Data

[62] Division of Ser. No. 277,369, Jun. 25, 1981, Pat. No. 4,365,096.

[51] Int. Cl.$^3$ .............................................. C10M 1/20
[52] U.S. Cl. ............................................. 252/52 R
[58] Field of Search ..................................... 252/52 R

[56] References Cited

U.S. PATENT DOCUMENTS

3,370,080  2/1968  Bloch ............................. 585/361 X

FOREIGN PATENT DOCUMENTS

49-20571  5/1974  Japan ................................... 568/665
1291739  10/1972  United Kingdom ................ 568/665

*Primary Examiner*—Andrew Metz
*Attorney, Agent, or Firm*—Jack H. Park; Walter D. Hunter; Richard A. Morgan

[57] ABSTRACT

Alkyl-substituted bicycloalkyl ether compositions useful in the preparation of synthetic lubricant compositions are obtained by reacting an alkyl-substituted 2-norbornene with a monohydric alcohol in the presence of an acidic catalyst.

2 Claims, No Drawings

ALKYL-SUBSTITUTED BICYCLOALKYL ETHERS AS USEFUL LUBRICANTS AND LUBRICATING OILS CONTAINING SAID ETHERS

This is a division of application Ser. No. 277,369 filed June 25, 1981 and now U.S. Pat. No. 4,365,096.

BACKGROUND OF THE INVENTION

1. Field of the Invention

This invention relates to new alkyl-substituted bicycloalkyl ether compositions, and particularly to monoalkyl ethers of alkyl-substituted bicyclo (2.2.1) heptanols, which are useful in the preparation of valuable lubricant compositions, and to an efficient process for preparing the new ethers in high yields from alkyl-substituted norbornene compounds.

The invention specifically provides new and particularly useful monoalkyl ethers of alkyl-substituted bicyclo (2.2.1) heptanols which can be generically represented by the formula

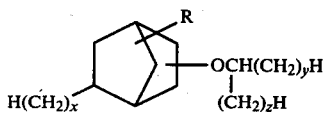

wherein R is hydrogen or methyl, x is an integer ranging from 4 to 18, y and z are integers ranging from 0 to 16 whose sum must be 8–16, and the sum of $x+y+z$ must be 20 to 36. The invention also provides an efficient process for preparing the new ethers which comprises reacting an alkyl-substituted norbornene with a monohydric alcohol in the presence of an acidic catalyst.

The new ethers of the invention possess valuable properties which make them suitable for use in important commercial applications, such as in the preparation of lubricant compositions. Because of their high boiling points, good stability and desired viscosity and lubricating properties the new ethers of this invention are particularly useful in the preparation of improved lubricant compositions.

2. Prior Art

Some ethers of bicyclo (2.2.1) heptanol have been prepared in the past, such as described in U.S. Pat. No. 3,370,080, by hydrating norbornene to form norbornane alcohol and reacting that secondary alcohol with an alkylene oxide. Such products have a polyoxyalkylene group which limits the oleophilic properties of the ethers. The oleophilic properties of the products of U.S. Pat. No. 3,370,080 are further restricted by the limitation on the size of the alkyl side chains as noted in that reference.

Further advantage of the present ether compositions over other types of known synthetic lubricant compositions, and particularly those of the ester type, include the improved resistance to alkali and hydrolysis of the ether linkage over the ester linkages of the known compounds. Additional advantage is also found in the fact that the new ether compositions can be prepared from inexpensive compounds, such as alphaolefins and cyclic diolefins, and obtained in high yield by a simple two-step process; thus presenting an economic advantage over many of the known synthetic lubricant compositions.

SUMMARY OF THE INVENTION

The ethers of the present invention comprise the monoalkyl ethers of alkyl-substituted bicyclo (2.2.1) heptanols and can be generically represented by the formula

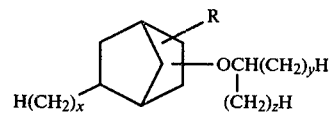

wherein R is hydrogen or methyl, x is an integer from 4 to 18, y and z are integers from 0 to 16 whose sum must be 8 to 22, and the sum of $x+y+z$ must be 20 to 36. The invention further provides an efficient process for preparing the new ethers in high yields which comprises reacting an alkyl-substituted norbornene with a monohydric alcohol in the presence of an acidic catalyst.

In view of their valuable properties, and particularly their high boiling points, good stability to alkali, and desired viscosity and lubricating properties, the new ethers of the invention are particularly suited for preparation of lubricant compositions, and the invention provides new and valuable lubricant compositions containing the said new ethers.

DESCRIPTION OF THE PREFERRED EMBODIMENTS

While R in the above-described formula is preferably hydrogen, it may also be methyl.

In the above-described formula x is an integer ranging from 4 to 18 yielding alkyl radicals which may be exemplified by butyl, hexyl, isohexyl, heptyl, octyl, dodecyl, tridecyl and tetradecyl radicals, and the like. Particularly preferred compounds are those wherein the x in the above-described formula ranges from 6 to 14 and the radicals contain from 6 to 14 carbon atoms.

In the above-described formula y and z are integers ranging from 0 to 16 whose sum must be 8 to 22 with the sum of $x+y+z$ equaling 20 to 36. Examples of hydrocarbon radicals which yield such configurations include, among others, 1-octyl, 1-decyl, 1-dodecyl, 1-ethylhexyl, 1-butyldodecyl, 1-amyltetradecyl, 1-propyldodecyl, 1-ethyldecyl, 1-hexyldodecyl, 1-heptyloctadecyl, 1-ethyleicosyl, octadecyl, tetradecyl, nonadecyl, eicosyl, 1-hexyldecyl, 1-hexyloctadecyl and the like, and mixtures thereof. Where branching in the radical is avoided (i.e., when z is equal to 0) unusual properties are imparted to the new ethers and such products represent a specially preferred group of ethers.

Particularly preferred ethers are those of the formula wherein R is hydrogen, x is an integer from 4 to 18, z is 0 to 8 and y is an integer from 14 to 22, with the total of $x+y+z$ equaling 20 to 36. Also of interest are those of the formula wherein R is hydrogen, x is an integer from 6 to 14, z is 0 and y is an integer from 14 to 30, with the total $x+y$ being 20 to 36.

The new monoalkyl ethers of alkyl-substituted bicyclo (2.2.1) heptanols of the present invention can be exemplified by the following:

5- and 6-tetradecyl bicyclo (2.2.1) heptyl decyl ether.
5- and 6-octyl bicyclo (2.2.1) heptyl tetradecyl ether.
5- and 6-octadecyl bicyclo (2.2.1) heptyl 1-butyldecyl ether.

5- and 6-dodecyl bicyclo (2.2.1) heptyl 1-octyldodecyl ether.

5- and 6-heptyl bicyclo (2.2.1) heptyl 1-dodecyltetradecyl ether.

5- and 6-butyl bicyclo (2.2.1) heptyl 1-tetradecyloctadecyl ether.

5- and 6-octylbicyclo (2.2.1) heptyl 1-amyloctadecyl ether.

5- and 6-dodecyl bicyclo (2.2.1) heptyl 1-octyldodecyl ether.

5- and 6-dodecyl bicyclo (2.2.1) heptyl 1-amyloctadecyl ether.

5- and 6-butyl bicyclo (2.2.1) heptyl eicosyl ether.

5- and 6-octyl bicyclo (2.2.1) heptyl 1-octylpentadecyl ether.

5- and 6-butyl bicyclo (2.2.10 heptyl 1-butyleicosyl ether.

Coming under special consideration are the alkyl ethers of 5- and 6-alkyl bicyclo (2.2.1) heptanols wherein the alkyl ether radical and the alkyl radical substituted on the bicyclo (2.2.1) heptanol molecule together contain from 20 to 36 carbon atoms.

The new compositions of the present invention can be prepared by a variety of methods but are preferably prepared by condensing an alpha-olefin with a cyclopentadiene or dicyclopentadiene as in a Diels-Alder type condensation reaction to form an alkyl-substituted norbornene, and then reacting the norbornene with the desired monohydric alcohol in the presence of an acidic catalyst. It was unexpected to find that the monohydric alcohols could be added to the alkyl-substituted norbornenes in the presence of the acidic catalyst to form the desired substituted norbornanes in view of certain disclosures in the prior art indicating that related acid catalyzed reactions with norbornenes resulted in many cases in a structural rearrangement. See, for example, Kock et al. Liebigs Ann. Chem. 638. 11 (1960).

The formation of the alkyl-substituted norbornenes by reacting an alpha-olefin with a cyclopentadiene or dicyclopentadiene can be illustrated by the following equation:

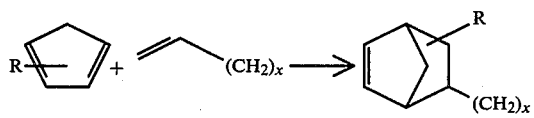

wherein R may be hydrogen or an alkyl radical as described above and the —(CH2)x radical may be as described above wherein x is an integer from 4 to 18. It is well known that the cyclopentadienes are in equilibrium with the corresponding dicyclopentadienes and the use of the dicyclopentadienes, as in some of the working examples at the end of the specification, is in effect addition of the cyclopentadiene as shown in the above equation.

The alpha-olefins used in the preparation of the alkyl-substituted norbornenes by the reaction shown above may be of any type but are preferably the 1-alkenes containing at least three carbon atoms, and preferably from 6 to 20 carbon atoms. Such olefins may be exemplified by 1-pentene, 1-hexene, 1-octene, 1-decene, 1-dodecene, 1-tetradecene, 1-octadecene, 1-eicosene, 3-butyloctene-1, 2 6-dimethyldodecene-1, 3-amyldodecene-1, and the like, and mixtures thereof. These olefins are preferably obtained by cracking hydrocarbon wax or by telomerizing ethylene.

The reaction between the alpha-olefin and the cyclopentadiene or dicyclopentadiene to form the alkyl-substituted norbornene as shown in the above equation can be accomplished by heating the components together in a sealed autoclave at a temperature generally ranging from about 150° C. to about 300° C., and more preferably at about 200° C. The pressure may vary as needed to help the reagents in the liquid state at the temperature selected and generally will range from about 1 to about 20 atmospheres. The components can be combined in a variety of different ratios varying from stoichiometric amounts up to an excess of either reactant. In general, it is preferred to utilize the alpha-olefin in large excess, e.g. from 2 to 6 molar excess. More specifically, molar ratios of cyclopentadiene to alpha-olefin may vary from about 1:1 to 1:5 as needed or desired. Solvents may be utilized as desired, but in many cases the excess alpha-olefin furnishes sufficient fluidity for the desired condensation reaction. The desired alkyl-substituted norbornenes can be recovered from the reaction mixture by any suitable means, such as distillation, solvent extraction, and the like.

In view of the different steric arrangements that may result from this type of condensation, the resulting products will generally be a mixture of endo and exo derivatives as represented by the following illustration of the structure of endo-5-butyl-2-norbornene and exo-5-butyl-2-norbornene:

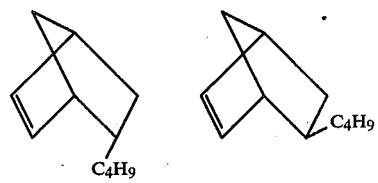

Examples of these mixtures of steric isomers include, among others, a mixture of endo-5-octyl and exo-5-octyl-2-norbornene, mixture of endo-5-dodecyl and exo-5-dodecyl-2-norbornene, a mixture of endo-5-tetradecyl and exo-5-tetradecyl-2-norbornene, a mixture of endo-5-heptyl and exo-5-heptyl-2-norbornene, and a mixture of endo-5-octyl and 6-octyl-2-norbornene. These isomers have closely-related boiling points and react substantially the same in the formation of the new products of the invention so they can be used as a mixture without further separation.

The alkyl-substituted norbornenes prepared as above are then reacted with a monohydric alcohol to form the desired monoalkyl ether of the alkys-substituted norbornane. This reaction can be illustrated by the following equation:

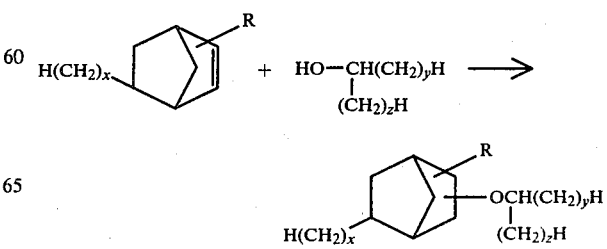

wherein R, x, y and z are as described above for the generic formula representing the compounds of the present invention.

The monohydric alcohols to be reacted with the substituted norbornenes may be any primary or secondary monohydric hydrocarbon alcohol having the prescribed number of carbon atoms as set out in the generic formula. Examples of such alcohols include, among others, 1-butanol, 2-pentanol, 2-hexanol, 1-octanol, 1-ethylhexanol-1, 1-heptyloctanol-1, 1-tetradecanol, 1-eicosanol, 1-pentyldodecanol-1, 1-octyloctadecanol-1, 1-ethyleicosanol-1, 1,3,5-tributyldodecanol-1, 1-butyl-2-isohexyltetradecanol-1, and 1-isohexyl-tetradecanol-1, and mixtures thereof. Particularly preferred are the normal alkanols and the secondary 1-alkylalkanols containing from 4 to 20 carbon atoms.

The reaction is accomplished by heating the alkyl-substituted norbornene with the monohydric alcohol in the presence of an acidic catalyst. The acidic catalyst employed may be any of the known Friedel-Crafts or Lewis acid type catalysts. Such catalysts include, among others, boron trifluoride complexes, such as their ether complexes, hydrofluoric acid, aluminum chloride, tin chloride, ion-exchange resins, such as Amberlyst ® 15, a cross-linked styrene-sulfonic acid resin manufactured by the Rohm and Hass Co., and Nafion ®, a polyfluoro carbon supported perfluoro sulfonic and resin manufactured by E. I. du Pont de Nemours and Co., etc., and mixtures thereof. Preferred catalysts include boron trifluoride and its complexes, and particularly its complexes with ethers, such as, for example, boron trifluoride diether complex, boron trifluoride dipropyl ether complex, boron trifluoride cyclohexyl ether complex, boron trifluoride benzyl ether complex, and boron trifluoride dicyclopentenyl ether complex, and the like, and mixtures thereof. Suitable substitutes include the corresponding boron tribromide and boron triiodide complexes. The amount of the acidic catalyst employed may vary over a wide range depending upon the catalyst selected, reactants and conditions. In general, the catalyst will vary from about 0.01% to 10% by weight of the reactants, and more preferably from about 0.1% to 5% by weight of reactants.

The proportion of the alkyl-substituted norbornene and the monohydric alcohol to be used in the reaction mixture may vary over a wide range. In most cases, it is desirable to utilize the above components in about stoichiometric amounts although it is sometimes convenient to utilize an excess of either reactant. In general, reactants are employed in molar ratios varying from about 1.5:1 to 1:1.5.

Preferably, the reactants can be combined by themselves, however, inert solvents or diluents may be utilized as needed or desired.

The temperature employed in the reaction between the substituted norbornene and the monohydric alcohol may vary over a wide range depending upon the catalyst selected, nature of the reactants and reaction rate desired. In most cases, the temperature will vary from about 100° C. to 200° C., and still more preferably from 100° C. to 150° C. Pressures may also be varied as needed to keep the reactants in a liquid state at the temperature selected and generally will range from about 1 to about 20 atmosphere. It is generally preferred to conduct the reaction in an inert atmosphere, such as in the presence of nitrogen.

The desired ether products can be recovered from the reaction mixture by any suitable means, such as distillation, solvent extraction, and the like. Preferably the unreacted components as well as the product are recovered by reduced pressure distillation, leaving the desired ether as bottoms product.

The alkyl-substituted bicycloalkyl ethers of the present invention will vary from liquids to soft solids and will be soluble in a variety of solvents. They possess valuable properties which make them suitable for use in important applications, such as in the preparation of lubricant compositions and plasticizing agents. The new ethers are particularly useful in the preparation of synthetic lubricants because of their high boiling points, good stability and desired viscosity and lubricating properties. In this application, they may be used as such or added as components for other lubricating products, such as other hydrocarbon liquid lubricants or other synthetic polyester lubricant compositions.

To illustrate the preparation of the new ethers and their properties, the following examples are given. It is to be understood, however, that the examples are given in the way of illustration and are not to be regarded as limiting the invention in any way.

EXAMPLE I

This example illustrates the preparation and some of the properties of 5- and 6-octyl bicyclo (2.2.1) heptyl tetradecyl ether.

1-decane (5984 g) and dicyclopentadiene (770 g. technical grade) were placed in a sealed autoclave and heated to 220° C. for a period of about 3 hours. The reaction mixture was then distilled to give a mixture of exo- and endo-5-octyl-2-norbornene.

1-tetradecanol (30.0 g) the mixture of exo- and endo-5-octyl-2-norbornene (88 g) produced above and of Nafion ® resin catalyst (5.0 g) were placed in a 300 ml rocking autoclave fitted with a glass liner, under nitrogen atmosphere and reacted at 120° C. for a period of about six hours. After cooling to room temperature, the reaction mixture was separated from solid catalyst by filtration. The unreacted 5-octyl-2-norbornene and 1-tetradecanol were removed by distillation leaving the 5- and 6-octyl bicyclo (2.2.1) heptyl tetradecyl ether as bottoms product. The ether recovered in yield of 40.09 grams had a viscosity index of 138. The structure was identified by nuclear magnetic spectra. Addition of the ether to conventional lube stock gives a lubricant composition having good stability and lubricating properties.

EXAMPLE II

This example illustrates the preparation and properties of 5- and 6-hexyl bicyclo (2.2.1) heptyl octadecyl ether.

1-octene (1400 g) and dicyclopentadiene (280 g. technical grade) were reacted in a sealed autoclave at 220° C. over a period of three hours. The reaction mixture was then distilled to give a mixture of exo- and endo-5-hexyl-2-norbornene.

1-octadecanol (37.8 g), the mixture of exo- and endo-5-hexyl-2-norbornene (32 g) produced above and of Nafion ® resin catalyst (5 g) are placed in a 300 ml rocking autoclave as in the preceding example and reacted under nitrogen at a temperature of 120° C. for a period of about six hours. After cooling to room temperature, the reaction product is separated from the solid catalyst by filtration. The unreacted exo- and endo-5-hexyl-2-norbornene and 1-octadecanol are removed by distillation leaving the desired 5- and 6-hexyl bicyclo (2.2.1) heptyl octadecyl ether. Addition of the new ether to conventional lube stock gives a lubricant having improved lubricating properties.

EXAMPLE III

This example illustrates the preparation of 5- and 6-octyl bicyclo (2.2.1) heptyl 1-butyldecyl-1 ether.

1-butyldecanol-1 (30 g), the mixture of exo- and endo-5-octyl-2-norbornene (38 g) produced in Example I and Nafion ® resin catalyst (5 g) are placed in a 300 ml rocking autoclave and heated under nitrogen for about six hours at 120° C. After cooling to room temperature, the reaction mixture is spearated from solid catalyst by filtration. The unreacted 5-octyl-2-norbornene and 1-butyldecanol-1 are removed by distillation leaving the 5- and 6-octyl bicyclo (2.2.1) heptyl 1-butyldecyl-1 ether as bottoms product.

Addition of the above-described ether to lub stock gives a lubricant composition having improved lubricating properties.

EXAMPLE IV

Example I is repeated with the exception that the mixture of exo- and endo-5-octyl-2-norbornene is replaced with equivalent amounts of each of the following: exo- and endo-5-decyl-2-norbornene, exo- and endo-5-dodecyl 2-norbornene and exo- and endo-5-tetradecyl-2-norbornene. Related results are obtained.

EXAMPLE V

Examples I, II and III are repeated with the exception that the Nafion ® resin is replaced by an equivalent amount of boron trifluoride diethyl ether complex. Related results are obtained.

I claim as my invention:

1. A lubricant composition comprising a major proportion of a mixture of 5- and 6-octyl bicyclo (2,2,1) heptyl tetradecyl ether.

2. A lubricant composition comprising a major proportion of an oil of lubricating viscosity and in an amount to improve the lubricating properties thereof of an ether of the formula:

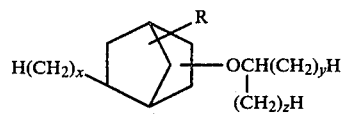

wherein R is selected from the group consisting of hydrogen and methyl, x is an integer ranging from 4 to 18, y and z are integers ranging from 0 to 16 whose sum must be 8 to 22 and the sum of $x+y+z$ must be 20 to 36.

* * * * *